United States Patent [19]

Kitaura et al.

[11] Patent Number: 4,460,502
[45] Date of Patent: Jul. 17, 1984

[54] PEPTIDE, PROCESS FOR PREPARATION THEREOF AND USE THEREOF

[75] Inventors: Yoshihiko Kitaura, Sakurai; Osamu Nakaguchi, Toyonaka; Keiji Hemmi, Suita; Satoshi Yonishi, Kadoma; Hidekazu Takeno, Tenri; Satoshi Kada, Takatsuki; Masashi Hashimoto, Takarazuka, all of Japan

[73] Assignee: Fujisawa Pharmaceutical Co., Ltd., Osaka, Japan

[21] Appl. No.: 316,653

[22] Filed: Oct. 30, 1981

[30] Foreign Application Priority Data

Nov. 11, 1980 [GB] United Kingdom ............... 8036175
Apr. 21, 1981 [GB] United Kingdom ............... 8112290

[51] Int. Cl.$^3$ ........................................... C07C 103/52
[52] U.S. Cl. ........................................... 260/112.5 R
[58] Field of Search .................. 424/177; 260/112.5 R

[56] References Cited

U.S. PATENT DOCUMENTS 4,261,979  4/1981  Jolles et al. .................. 260/112.5 R
4,311,640  1/1982  Kuroda et al. ............... 260/112.5 R

FOREIGN PATENT DOCUMENTS 2033906  5/1980  United Kingdom .
2053231  2/1981  United Kingdom .

OTHER PUBLICATIONS

Dezelee et al., *Biochemistry*, vol. 9, No. 4, 1970, pp. 823–831.
Kitaura et al., "European Patent Application", Ser. No. 11,283, 5/20/80.
Schröder, *The Peptides*, vol. 1, Academic Press, New York, 1965, p. xxvii.
March, *Advanced Organic Chemistry*, 2nd Ed., N.Y., McGraw-Hill Book Co., 1977, pp. 246–259.
Ariëns, *Drug Design*, vol. II, N.Y., Academic Press, 1971, pp. 338–341, 355, 360–362.
Biochemistry, vol. 9, No. 4, 1970, pp. 823–831, (Dezelee et al.).
Biochemical and Biophysical Research Communications, vol. 59, No. 4, 1979, pp. 1317–1325, (Ellouz et al.).
Agricultural and Biological Chemistry, 41(5), 1977, pp. 763–768, (Nakamura et al.).
Abstracts of the Eleventh International Congress on Chemotherapy, Oct. 1–5, 1979, Abstract-702, (Werner et al.).
11th International Congress of Chemotherapy, 19th Interscience Conference on Antimicrobial Agents and Chemotherapy, Oct. 1979, Werner et al, Immunopotentiating Activities of Microbial Tetrapeptides after Coupling with Lauric Acid.

*Primary Examiner*—Delbert R. Phillips
*Assistant Examiner*—F. T. Moezie
*Attorney, Agent, or Firm*—Oblon, Fisher, Spivak, McClelland & Maier

[57] ABSTRACT

The invention deals with novel peptides useful for the therapeutic treatment of infectious diseases caused by pathogenic microorganisms, having the structure

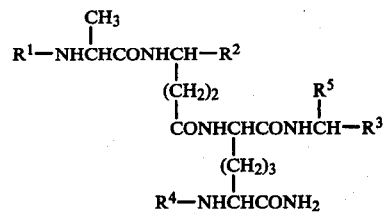

wherein
$R^1$ is substituted or unsubstituted lower alkanoyl, or substituted or unsubstituted aralkanoyl,
$R^2$ and $R^3$ are each carboxy or protected carboxy,
$R^4$ is hydrogen or an amino protective group, and
$R^5$ is hydrogen or lower alkyl, and their pharmaceutically acceptable salts.

8 Claims, No Drawings

PEPTIDE, PROCESS FOR PREPARATION THEREOF AND USE THEREOF

This invention relates to a new peptide. More particularly, this invention relates to a new peptide and the pharmaceutically acceptable salt thereof, which have pharmacological activities, to processes for the preparation thereof and to a new intermediate for preparing the active peptide, and to the pharmaceutical composition comprising the same and a method of use thereof.

A new peptide of this invention is represented by the following formula (I):

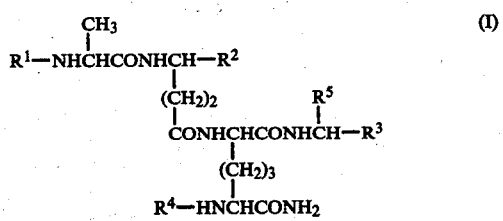

wherein
$R^1$ is substituted or unsubstituted lower alkanoyl, or substituted or unsubstituted aralkanoyl,
$R^2$ and $R^3$ are each carboxy or protected carboxy,
$R^4$ is hydrogen or an amino protective group, and
$R^5$ is hydrogen or lower alkyl.

Particulars of the various definitions, which are mentioned hereinabove and hereinafter, and preferred examples thereof are explained in the following.

The term "lower" is intended to mean a group having 1 to 8 carbon atoms, unless otherwise provided.

(1) Re. Substituted or unsubstituted lower alkanoyl for $R^1$:

As suitable examples of unsubstituted lower alkanoyl, there may be exemplified formyl, acetyl, propionyl, butyryl, isobutyryl, valeryl, isovaleryl, pivaloyl, hexanoyl, α-ethylhexanoyl, heptanoyl, octanoyl and the like.

As substituted lower alkanoyl, there may be exemplified lower alkanoyl as illustrated above which is substituted by one or more suitable substituent(s) such as amino, halogen (e.g. fluorine, chlorine, bromine, etc.), hydroxy, carboxy and the like, and among substituted lower alkanoyl, there may be exemplified hydroxy (lower) alkanoyl such as 2-hydroxypropionyl (i.e. lactoyl) as more suitable example.

In the above exemplified substituted lower alkanoyl in case that these lower alkanoyl has one or more functional group(s) such as hydroxy, amino and carboxy, such a functional group may be protected by a conventional protective group.

(2) Re. Substituted or unsubstituted aralkanoyl for $R^1$:

As a suitable unsubstituted aralkanoyl, there may be exemplified ar(lower) alkanoyl such as mono or diphenyl(lower)alkanoyl (e.g. phenylacetyl, diphenylacetyl, etc.) and the like.

As a suitable substituted aralkanoyl, there may be exemplified ar(lower)alkanoyl, arene and (or) alkane moiety of which is substituted by one or more suitable substituent(s) such as the same as those exemplified as the suitable substituent for substituted lower alkanoyl for $R^1$.

Among said substituted aralkanoyl, as suitable example there may be exemplified ar(lower)hydroxyalkanoyl such as mandelyl and the like.

In the above exemplified substituted aralkanoyl, in case that these aralkanoyl has one or more functional group such as hydroxy, amino and carboxy, such a functional group may be protected by a conventional protective group.

(3) Re. Protected carboxy for $R^2$, $R^3$, and $R_a^3$, and functional group in the group for $R^1$:

A protective group of the protected carboxy includes a conventional carboxy protective group which is conventionally used in the field of amino acid and peptide chemistry.

As suitable examples of protected carboxy, there may be exemplified an ester such as an ester with silyl compound, an ester with an aliphatic hydroxy compound and an ester with a hydroxy compound containing an aromatic group.

As more suitable examples of protected carboxy, there may be exemplified aralkyl (e.g. benzyl, diphenylmethyl, etc.) ester and the like.

(4) Re. Amino protective group for $R^4$, $R_a^4$ and $R_b^4$, and functional group in the group for $R^1$:

The amino protective group includes a conventional amino protective group which is used in the field of amino acid and peptide chemistry.

As suitable examples of the amino protective group, there may be exemplified alkoxycarbonyl (e.g. methoxycarbonyl, ethoxycarbonyl, propoxycarbonyl, butoxycarbonyl, t-butoxycarbonyl, t-pentoxycarbonyl, etc.), aralkoxycarbonyl (e.g. benzyloxycarbonyl, etc.) and the like.

(5) Re. Hydroxy protective group in the group for $R^1$:

As suitable example of a hydroxy protective group in substituted lower alkanoyl and substituted aralkanoyl for $R^1$, there may be exemplified a conventional one, for example, acyl such as alkanoyl (e.g. acetyl, etc.).

(6) Re. Lower alkyl for $R^5$:

Suitable example of lower alkyl for $R^5$ is one having 1 to 6 carbon atoms such as methyl, ethyl, propyl, isopropyl, butyl, isobutyl, pentyl, isopentyl and the like.

A pharmaceutically acceptable salt of the new peptides of the formula (I) may include a salt with an inorganic or organic base such as an alkali metal salt (e.g. sodium salt, potassium salt, etc.), an alkaline earth metal salt (e.g. calcium salt, etc.), ammonium salt, organic amine salt (e.g. ethanolamine salt, triethylamine salt, dicyclohexylamine salt, etc.) or the like, and an acid addition salt with organic or inorganic acid such as methane sulfonate, hydrochloride, sulfate, nitrate, phosphate or the like. The compound (I) of this invention can be prepared by various methods, details of which will be apparent from the following descriptions.

(1) Process 1: Peptide bond formation

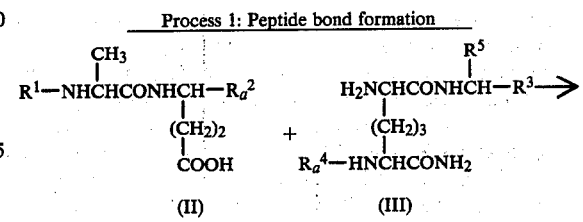

-continued

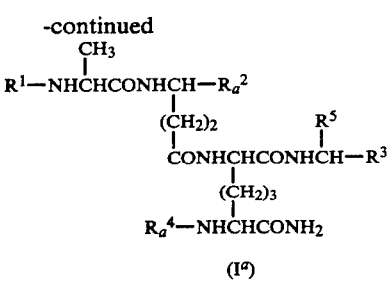
(Iª)

(2) Process 2: Elimination of protective groups

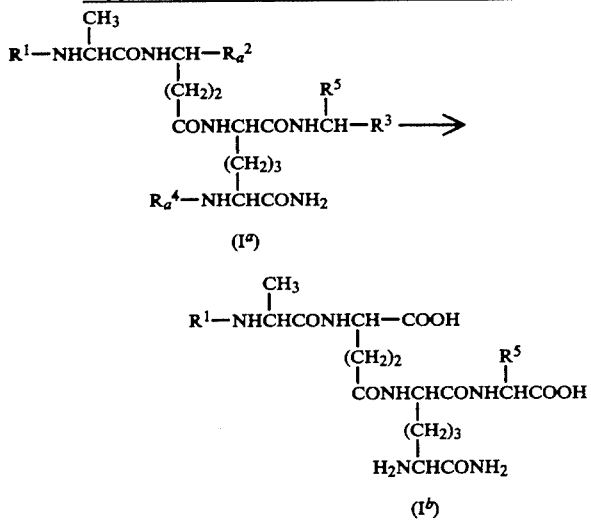

In the above formula, $R^1$, $R^3$ and $R^5$ are each as defined above, $R_a^2$ is protected carboxy, and $R_a^4$ is amino protective group.

Detailed explanation of processes for preparing of the compound (I) will be made in the following:

(1) Process 1: Peptide bond formation Compound (II) + Compound (III) → Compound (Ia)

This process relates to a method for preparing Compound (Ia) by reacting Compound (II) or its salt with a Compound (III) or its salt.

The reaction of this process can be conducted as follows.

That is, in one case, as the first step, the carboxy group of Compound (II) or its salt is usually activated in a conventional manner, for example, in the form of its acid halide, azide, acid anhydride or a mixed anhydride, activated ester, and the like, and is reacted with the Compound (III) to give Compound (Ia), and in the other case, the Compound (II) or its salt is reacted with the Compound (III) or its salt directly in the presence of a conventional condensing agent such as N,N-dicyclohexylcarbodiimide and the like. Among these activation methods, preferred activation method for the carboxy group of the Compound (II) into its activated form and preferred condensing agent as mentioned above are selected according to kinds of the carboxy protective group(s) of the Compound (II) and (III) and to the reaction conditions (e.g. the kinds of the reaction solvent, reaction temperature and so on).

This reaction is preferably carried out in a solvent such as methylene chloride, chloroform, tetrahydrofuran, dioxane, ethyl acetate, methanol, ethanol, water or the like under at $-20°$ C. to at ambient temperature and the reaction in the presence of a condensing agent is usually carried out in an anhydrous, but not critical conditions.

(2) Process 2: Elimination of protective group(s) Compound (Iª) → Compound (Iᵇ)

This process relates to a method for preparing Compound (Iᵇ) by subjecting Compound (Iª) to elimination reaction of protective group(s) of protected carboxy for $R_a^2$ and (or) $R^3$, and (or) an amino protective group for $R^4$, detailed explanation for which is as follows:

Process 2-1: Elimination of an amino protective group for $R^4$

This process can be applied to case that the amino protective group for $R^4$ reveals a chemically different behavior from that of the acyl group for $R^1$ against each kind of the elimination methods to be employed, that is, the case that the amino protective group can be eliminated, but the acyl group for $R^1$ is not eliminated according to the elimination method as employed.

This reaction is carried out by conventional methods such as catalytic reduction method, liquidammoniaalkalimetal method, acid method, zinc acid method, base method, hydrazine method and the like.

Among these methods, preferred one is selected according to kind of the amino protective group for $R^4$, and also to the chemically different behavior of said amino protective group from the acyl for $R^1$ as explained above.

Among the above elimination methods, an acid method is employed as the most convenient and conventional one and said method is explained as follows:

This reaction is conventionally carried out in a solvent such as methylene chloride, chloroform, acetic acid, water and the like in the presence of inorganic or organic acid such as trifluoroacetic acid, formic acid, p-toluenesulfonic acid, hydrochloric acid, hydrobromic acid and the like and anisole is preferably added thereto.

Among the exemplified acid, trifluoroacetic acid and formic acid are also used as the solvent.

This reaction is usually carried out under ice-cooling to an ambient temperature.

Process 2-2: Elimination of carboxy protective group of protected carboxy for $R_a^2$ and $R^3$ The reaction for elimination of protective group of the protected carboxy group is carried out by a conventional method such as hydrolysis and reduction or the like, details of which are explained in the following.

(i) For hydrolysis which refers to the same meaning as solvolysis including, for example, acidolysis, alcoholysis, aminolysis, hydroxinolysis, etc.:

Hydrolysis is preferably carried out in the presence of an acid or base.

Suitable acid includes an inorganic acid (e.g. hydrochloric acid, hydrobromic acid, sulfuric acid, etc.), an organic acid (e.g. formic acid, acetic acid, trifloroacetic acid, propionic acid, benzenesulfonic acid, p-toluenesulfonic acid, etc.), an acidic ion exchange resin and the like.

Suitable base includes an inorganic base such as alkali or alkaline earth metal hydroxide or the corresponding carbonate or bicarbonate (e.g. sodium hydroxide, potassium hydroxide, sodium carbonate, potassium carbonate, lithium carbonate, sodium bicarbonate, calcium hydroxide, magnesium hydroxide, etc.), ammonium hydroxide or the like; an organic base such as an alkoxide or phenoxide of the above metal (e.g. sodium ethoxide, sodium methoxide, lithium phenoxide, etc.), an amine such as mono-, di- or trialkylamine (e.g. methylamine, ethylamine, propylamine, isopropylamine, butyl-amine, N,N-dimethyl-1,3-propanediamine, trimethylamine, triethylamine, etc.), unsubstituted, mono- or disubstituted arylamine (e.g. aniline, N-methylaniline, N,N-dimethylaniline, etc.), a heterocyclic base (e.g. pyrrolidine, morpholine, N-methylmorpholine, N-methylpiperidine, N,N-dimethylpiperazine, pyridine, etc.), hydrazines (e.g. hydrazine, methylhydrazine, ethylhydrazine, etc.) or the like; a basic ion-exchange resin and the like.

The hydrolysis is preferably conducted under somewhat milder conditions such as cooling or warming and usually in a solvent which does not have adverse influence to the reaction, e.g. water, a hydrophilic solvent such as alcohol (e.g. methanol, ethanol, propanol, etc.), acetone, N,N-dimethylformamide, tetrahydrofuran, dioxane, dimethylsulfoxide, etc. or a mixture thereof, and other hydrophobic solvent such as benzene diethylether, etc. may also be used as a solvent. A liquid abovementioned acid or base can also be used as solvent.

(ii) For reduction:

Reduction, including chemical reduction and catalytic reduction, is carried out in a conventional manner.

Suitable reducing agents to be used in chemical reduction are a metal (e.g. tin, zinc, iron, etc.), or a combination of such metal and/or metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g. platinum plate, spongy platinum platinum black, colloidal platinum, platinum oxide or platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc.) or the like.

The reduction is usually carried out in a solvent. A suitable solvent to be used may be, e.g. water, alcohol (e.g. methanol, ethanol, propanol, etc.) and other conventional organic solvent or a mixture thereof. Additionally, the afore-mentioned liquid acids to be used in chemical reduction can also be used as solvent. Further, a suitable solvent to be used in catalytic reduction may be, e.g. the above-mentioned solvent, and other conventional solvent, such as diethyl ether, dioxane, tetrahydrofuran, etc. or a mixture thereof.

The reaction is preferably carried out under somewhat milder conditions such as cooling or warming.

Among these methods for elimination of protective groups, preferred one and appropriate combination methods are to be selected according to kinds of the protective groups of carboxy group and amino protective group to be removed off.

It is noted that this process includes the following cases of elimination of protective groups of protected carboxy and amino protective group, that is, one case that all of the carboxy protective groups for $R_a^2$ and $R^3$ and the amino protective group for $R^4$ in the Compound ($I^a$) are simultaneously removed by a method to be employed to the reaction, and the other case that the carboxy protective groups and the amino protective group are sequentially and stepwise removed by a method which is appropriately selected according to the kinds of the protective group to be removed.

As to Process 2 for elimination of protective group(s) (i.e. Process 2-1 and 2-2), the followings are to be noted. That is, in case that substituted or unsubstituted lower alkanoyl, or substituted or unsubstituted aralkanoyl group for $R^1$ has one or more protective group(s) for hydroxy, amino and (or) carboxy, such an amino protective group and carboxy protective group among said protective group may be simultaneously removed in this process, and such a hydroxy protective group such as alkanoyl (e.g. acetyl, etc.) may be previously removed by subjecting the compound ($I^a$) to elimination reaction of hydroxy protective group in a conventional manner such as reduction as illustrated in the Process 2-2.

The starting compounds (II) and (III) can be prepared by methods as follows:

(1) Process $1^s$

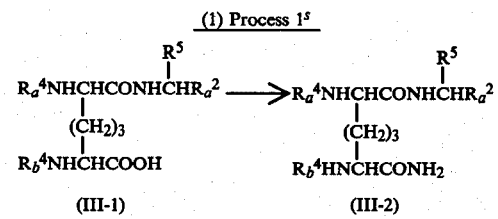

(2) Process $2^s$

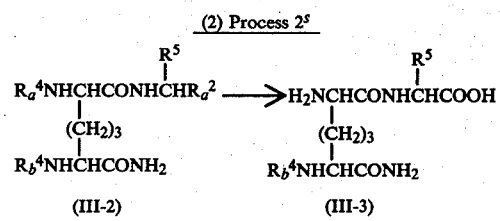

In the above formulae, $R_b^4$ is an amino protective group, and $R_a^2$, $R_a^4$ and $R^5$ are as defined above. (1) Process $1^s$: Compound (III-1)→Compound (III-2)

This process relates to a method for preparing compound (III-2) by subjecting Compound (III-1) to amidation reaction.

The reaction is usually carried out as the first step by activating the carboxy group of the compound (III-1) in a conventional manner, for example, in a form of its activated ester, and then reacting the resulting compound with ammonia.

This reaction is preferably carried out in a solvent such as methylene chloride, chloroform or the like under ice-cooling to at ambient temperature.

(2) Process $2^s$: Compound (III-2)→Compound (III-3)

This process relates to a method for preparing compound (III-3) by subjecting compound (III-2) to elimination reaction of protective group of protected carboxy for $R_a^2$.

This reaction is carried out substantially in the same manner as that of Process 2-2.

As to the object compound (I) and starting compounds (II) and (III) which are prepared according to the aforementioned Processes, it is to be noted that each of said compounds includes one or more stereoisomers which is due to the asymmetric carbon atoms in their molecule and all of such isomers are included within the scope of this invention.

The new peptide (I) and its pharmaceutically acceptable salts of this invention have been found to possess protective efficacy in experimental infection.

Accordingly, the new peptide (I) and its pharmaceutically acceptable salts are useful for the therapeutic treatment of infectious diseases caused by pathogenic microorganism, especially gram-negative bacteria and gram-positive bacteria and fungi.

Further, Compounds (II) and (III) are useful as intermediate for preparing Compound (I) having biologically active properties as mentioned above.

For the purpose of showing pharmaceutical utility of the new peptide (I), pharmacological test data thereof are illustrated in the following.

PROTECTIVE EFFICACY IN EXPERIMENTAL INFECTION IN MICE

In determining the protective efficacy against experimental infections in mice, the test compound was dissolved in and diluted with sterile saline to provide prescribed concentrations of drug.

Male ICR-strain mice, aged 4 weeks were used in groups of ten mice. E. coli 22 was cultivated overnight at 37° C. on trypticase soy agar and then were suspended in a sterile saline to obtain microbial cell concentration of $2.6 \times 10^9$ CFU/ml. Mice were inoculated intraperitoneally with $8.7 \times 10^7$ CFU/mouse. Each of the test drugs was given intraperitoneally in various doses to a group of ten mice four days before challenge.

Survival percent were found from the number of the surviving animals after three days of injection. Results are shown in Table

|                          | Survival (%)       |                     |          |
|--------------------------|--------------------|---------------------|----------|
| Test Compound (Example NO.) | Dose 0.1 mg/kg | Dose 0.01 mg/kg | Dose 0 |
| Example 1 (Step 2)       | 50                 | 100                 | 10       |
| Example 2 (Step 2)       | 80                 | 30                  | 30       |
| Example 3 (Step 2)       | 90                 | 70                  | 30       |

The pharmaceutical composition of this invention can be used in the form of a pharmaceutical preparation, for example, in solid, semisolid or liquid form, which contains an active substance of this invention in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, collidal silica, potato starch, urea and other carriers suitable for use in manufacturing preparations, in solid, semisolid, or liquid form, and in addition auxiliary, stabilizing, thickening and coloring agents and perfumes may be used. The pharmaceutical compositions can also contain preservative or bacteriostatic agents to keep the active ingredient in the desired preparations stable in activity. The active object compound is included in the pharmaceutical composition in an amount sufficient to produce the desired therapeutic effect upon the process or condition of diseases.

For applying this composition to humans, it is preferably to apply it by intravenous, intramuscular or oral administration. While the dosage or therapeutically effective amount of the object compound of this invention varies from and also depends upon the age and condition of each individual patient to be treated, a daily dose of about 0.1-100 mg of the active ingredient/kg of a human being or an animal is generally given for treating diseases, and an average single dose of about 50 mg, 100 mg, 250 mg, and 500 mg is generally administered.

The following examples are given for purpose of illustrating this invention.

In the following examples, starting compounds and object compounds are expressed by using the following abbreviations:

Lac: Lactoyl
Ala: Alanyl
Glu: Glutamyl
Gly: Glycyl
DAP: α, ε-Diaminopimelyl
Z: benzyloxycarbonyl
Boc: t-butoxycarbonyl
Bzl: benzyl
Ac: acetyl Preparation 1

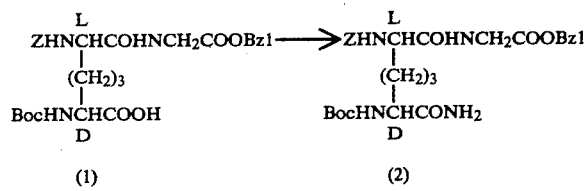

(1)           (2)

To a mixture of Z-(L)-Boc-(D)-mesoDAP-(L)-GlyOBzl (1)(3.95 g) and N-methylmorphorine (0.85 g) in dry methylene chloride (70 ml) was added isobutyl chloroformate (0.95 g) at $-10° \sim -15°$ C. and the mixture was stirred for 30 minutes at the same temperature. The mixture was then cooled to $-40°$ C. and 2N solution (15 ml) of ammonia in ethanol was added. After stirring for 30 minutes at the same temperature, the mixture was concentrated and the residue was dissolved in ethyl acetate, washed with water, dried over magnesium sulfate, and evaporated to give an oil, which was pulverized with ether to give Z-(L)-Boc-(D)-mesoDAP-(D)-NH$_2$-(L)-GlyOBzl (2)(3.1 g).

IR (Nujol): 3300, 1735, 1685, 1655 cm$^{-1}$.

NMR (CD$_3$OD): δ1.48 (9H, s), 1.4-2.0 (6H, m), 4.03 (2H, s), 3.9-4.3 (2H, m), 4.13 (2H, s), 4.22 (2H, s), 7.40 (10H, s).

Preparation 2

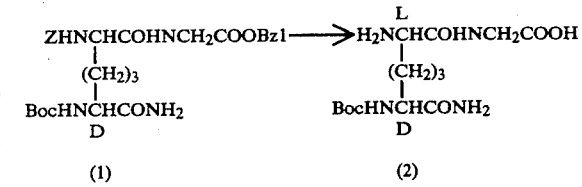

(1)           (2)

To a solution of Z-(L)-Boc-(D)-mesoDAP-(D)-NH$_2$-(L)-GlyOBzl (1)(2.7 g) in a mixture of methanol (75 ml) and water (10 ml) was added 10% palladium-charcoal (1.0 g) and the mixture was hydrogenated under an atmospheric pressure of hydrogen. After removal of the catalyst, the filtrate was evaporated to dryness. The residue was pulverized with ether to give Boc-(D)-mesoDAP-(D)-NH₂-(L)-GlyOH (2)(1.59 g).

IR (Nujol): 3600-2200, 1690 (sh), 1670 cm⁻¹.

NMR (CD₃OD): δ1.42 (9H, s), 1.2-2.0 (6H, m), 3.6-4.1 (4H, m).

EXAMPLE 1

(1) Step (1)

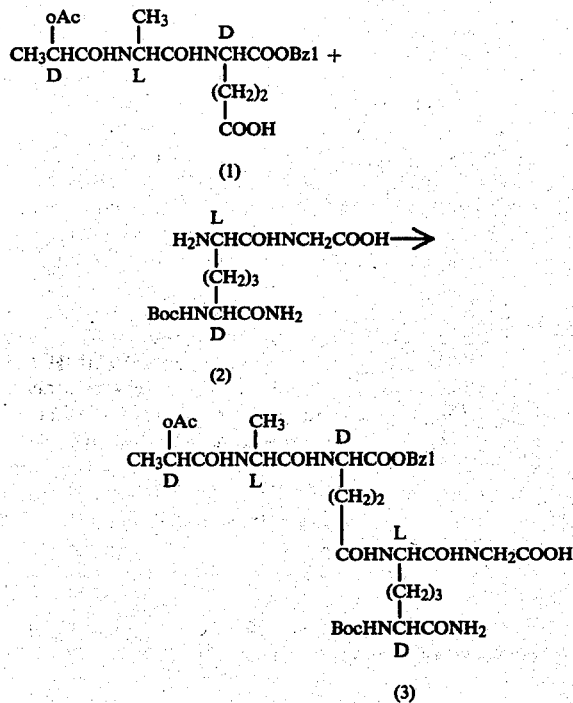

A mixture of D-Lac(oAc)-L-Ala-D-Glu(OH)OBzl (1) (1.15 g) and N-methylmorpholine (0.27 g) in methylene chloride (55 ml) was cooled to −15° C. and isobutyl chloroformate (0.37 g) was added dropwise. After stirring for 30 minutes at −10°∼15° C., the mixture was cooled to −40° C. and a solution of Boc-(D)-mesoDAP-(D)-NH₂-(L)-GlyOH (2)(0.94 g) and bis(-trimethylsilyl)acetamide (2.76 g) in methylene chloride (25 ml) was added. The mixture was stirred for 1.5 hours at −10°∼15° C. and for 1.5 hours at −15°∼0° C. The mixture was concentrated and the residue was dissolved in ethyl acetate (80 ml). The solution was washed successively with 2.5% hydrochloric acid and brine, dried over magnesium sulfate and evaporated to give a crystalline solid, which was washed with ether to give D-Lac(oAc)-L-Ala-γ-D-Glu(α-OBzl)-(L)-Boc-(D)-mesoDAP-(D)-NH₂-(L)-GlyOH (3)(1.80 g).

IR (Nujol): 3280, 1730, 1655, 1640 cm⁻¹.

NMR (CD₃OD): δ1.2-2.2 (25H, m), 2.12 (3H, s), 3.97 (2H, s), 4.2-5.0 (5H, m), 5.20 (2H, s), 7.39 (5H, s).

(2) Step 2

Compound (3) ⟶

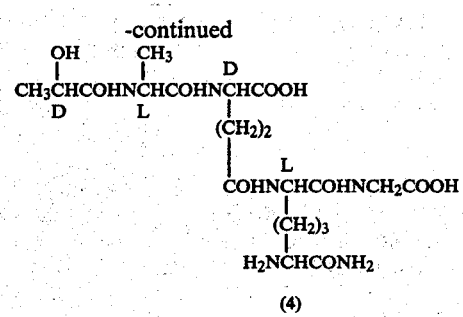

A solution of D-Lac-L-Ala-γ-D-Glu(α-OBzl)-(L)-Boc-(D)-mesoDAP-(D)-NH₂-(L)-GlyOH (3)(1.67 g) in a mixture of methanol (50 ml) and water (8 ml) was hydrogenated over 10% palladium-charcoal (1.0 g) under an atmospheric pressure of hydrogen. After removal of the catalyst, the filtrate was evaporated to dryness and the residue was dissolved in trifluoroacetic acid (15 ml) and stirred for 30 minutes at room temperature. After evaporation of trifluoroacetic acid, the residue was dissolved in 50% aqueous methanol (44 ml) and adjusted to pH 9 with 10% sodium carbonate. After stirring for 1 hour at room temperature, the mixture was concentrated and the resulting aqueous solution was adjusted to pH 2 with 5% hydrochloric acid and put on a column of an activated charcoal (30 ml). The column was washed with water and eluted with 80% aqueous methanol. The eluate was concentrated and the residue was chromatographed on a column of a macroporous non-ionic adsorption resin, HP-20 (230 ml), eluting with water. The eluate was concentrated and lyophilized to give D-Lac-L-Ala-γ-D-Glu(α-OH)-(L)-mesoDAP-(D)-NH₂-(L)-GlyOH (4)(0.81 g).

$[α]_D$ −34.4° (C=0.2, H₂O).

IR (Nujol): 3280, 1720 (sh), 1650 cm⁻¹.

NMR (D₂O): δ1.38 (3H, d, J=7 Hz), 1.42 (3H, d, J=7 Hz), 1.6-2.5 (10H, m), 3.96 (2H, s), 4.03 (1H, t, J=6 Hz), 4.2-4.5 (5H, m).

EXAMPLE 2

(1) Step 1

Heptanoyl-L-Ala-γ-D-Glu(α-OBzl)-(L)-Boc-(D)-mesoDAP-(D)-NH₂-(L)-D-AlaOH was prepared substantially in the same manner as step 1 of Example 1.

NMR (CD₃OD), δ: 0.93 (3H, t, J=5 Hz), 1.1-2.5 (35H, m), 3.9-4.6 (5H, m), 5.17 (2H, s), 7.35 (5H, s).

IR (Nujol) cm⁻¹: 3260, 1720, 1630, 1520, 1330, 1290, 1265, 1165.

(2) Step 2

Heptanoyl-L-Ala-γ-D-GLu(α-OH)-(L)-mesoDAP-(D)-NH₂-(L)-D-AlaOH was prepared substantially in the same manner as step 2 of Example 1.

NMR (D₂O), δ: 0.87 (3H, t, J=5 Hz), 1.37 (3H, d, J=7 Hz), 1.40 (3H, d, J=7 Hz), 1.1-2.5 (20H, m), 3.9-4.5 (5H, m).

IR (Nujol) cm³¹ ¹: 3280, 1690 (sh), 1640, 1540, 1230, 1165.

EXAMPLE 3

(1) Step 1

Phenylacetyl-L-Ala-γ-D-Glu(α-OBzl)-(L)-Boc-(D)-mesoDAP-(D)-NH₂-(L)-D-AlaOH was prepared substantially in the same manner as step 1 of Example 1.

NMR (CD₃OD), δ: 1.2-2.4 (25H, m), 3.56 (2H, s), 4.1-4.5 (5H, m), 5.14 (2H, s), 7.28 (5H, s), 7.34 (5H, s).

IR (Nujol) cm⁻¹: 3250, 1720, 1660, 1625, 1520, 1290, 1240, 1205, 1160.

(2) Step 2

Phenylacetyl-L-Ala-γ-D-Glu(α-OH)-(L)-mesoDAP-(D)-NH₂-(L)-D-AlaOH was prepared substantially in the same manner as step 2 of Example 1.

NMR (D₂O), δ: 1.32 (3H, d, J=6 Hz), 1.38 (3H, d, J=6 Hz), 1.4-2.2 (10H, m), 3.65 (2H, s), 3.8-4.5 (4H, m), 7.33 (5H, s).

IR (Nujol) cm⁻¹: 3270, 1640, 1530, 1240, 1160, 1025.

EXAMPLE 4

(1) Step 1

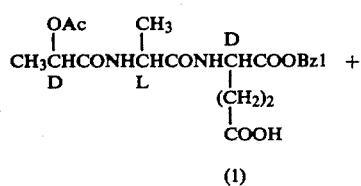

(1)

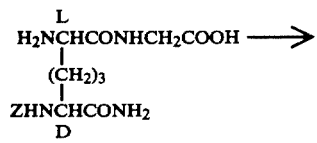

(2)

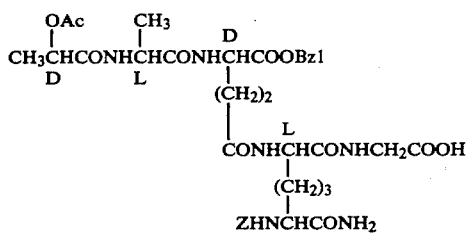

(3)

Isobutyl chloroformate (114 mg) was added to a mixture of D-Lac(OAc)-L-Ala-D-Glu(α-OBzl)OH (1) (351 mg) and triethylamine (84 mg) in methylene chloride (17 ml) at −10° to −15° C. and the mixture was stirred for 30 minutes at the same temperature. The mixture was then cooled to −40° C. and Z-(L)-mesoDAP-(D)-NH₂-(L)-GlyOH(2) trimethylsilyl ester, prepared from Z-(L)-mesoDAP-(D)-NH₂-(L)-GlyOH (316 mg) and bis(triemthylsilyl)acetamide (1.4 ml) by stirring in methylene chloride (8.5 ml), was added and the mixture was stirred for 5.5 hours at −10° to −15° C. After evaporation of the solvent, the residue was dissolved in ethyl acetate (80 ml) and washed with 2% hydrochloric acid (20 ml) and water (10 ml). Ethyl acetate was evaporated to dryness and the residue was pulverized with ether to give D-Lac(OAc)-L-Ala-γ-D-Glu(α-OBzl)-(L)-Z-(D)-mesoDAP-(L)-GlyOH-(D)-NH₂ (3) (457 mg). mp 172°-178° C. (dec).

IR (Nujol) cm⁻¹: 3380, 3250, 1740, 1715, 1660, 1640.

(2) Step 2

Compound (3) ⟶

-continued

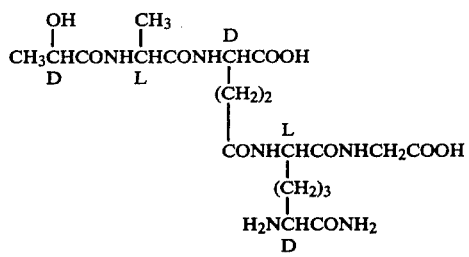

(4)

A solution of D-Lac(OAc)-L-Ala-γ-D-Glu(α-OBzl)-(L)-Z-(D)-mesoDAP-(L)-GlyOH-(D)-NH₂ (3) (400 mg) in acetic acid (40 ml) was hydrogenated over 10% palladium charcoal (100 mg). After removal of the catalyst, the filtrate was concentrated under reduced pressure. The residue was dissolved in 50% aqueous methanol (10 ml) and the mixture was stirred for 3 hours at room temperature, during which time pH of the mixture was maintained at 9 to 10 with 10% aqueous sodium carbonate. After removal of methanol, the the concentrate was acidified to PH 2 with 1N-hydrochloric acid. This solution was put on a column packed with HP 20 (100 ml) and eluted with water. The elute was concentrated to about 10 ml and lyophilized to give D-Lac-L-Ala-γ-D-Glu(α-OH)-(L)-mesoDAP-(L)-GlyOH-(D)-NH₂ (4) (210 mg).

NMR (D₂O), δ: 1.38 (d, J=7 Hz, 3H), 1.42 (d, J=7 Hz, 3H), 1.6-2.5 (m, 10H), 3.96 (s, 2H), 4.03 (t, J=6 Hz, 1H), 4.2-4.5 (m, 5H),

IR (Nujol) cm⁻⁴: 3280, 1720 (sh), 1650.

We claim:

1. A compound of the formula or its pharmaceutically acceptable salt:

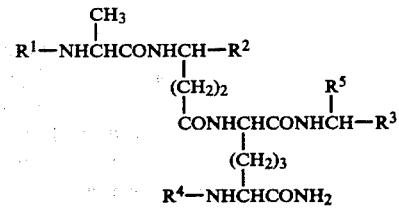

wherein
R¹ is heptanoyl, phenylacetyl, 2-hydroxypropionyl or 2-acetoxypropionyl,
R² is carboxy or benzyloxycarbonyl,
R³ is carboxy,
R⁴ is hydrogen, t-butoxycarbonyl or benzyloxycarbonyl, and
R⁵ is hydrogen or methyl.

2. A compound according to claim 1, wherein R¹ is 2-acetoxypropionyl, R² is benzyloxycarbonyl, R³ is carboxy, R⁴ is t-butoxycarbonyl and R⁵ is hydrogen.

3. A compound according to claim 1, wherein R¹ is 2-hydroxypropionyl, R² and R³ are each carboxy, R⁴ and R⁵ are each hydrogen.

4. A compound according to claim 1, wherein R¹ is heptanoyl, R² is benzyloxycarbonyl, R³ is carboxy, R⁴ is t-butoxycarbonyl and R⁵ is methyl.

5. A compound according to claim 1, wherein R¹ is heptanoyl, R² and R³ are each carboxy, R⁴ is hydrogen and R⁵ is methyl.

6. A compound according to claim 1, wherein $R^1$ is phenylacetyl, $R^2$ is benzyloxycarbonyl, $R^3$ is carboxy, $R^4$ is t-butoxycarbonyl and $R^5$ is methyl.

7. A compound according to claim 1, wherein $R^1$ is phenylacetyl, $R^2$ and $R^3$ are each carboxy, $R^4$ is hydrogen and $R^5$ is methyl.

8. A compound according to claim 1, wherein $R^1$ is 2-acetoxypropionyl, $R^2$ is benzyloxycarbonyl, $R^3$ is carboxy, $R^4$ is benzyloxycarbonyl and $R^5$ is hydrogen.

* * * * *

UNITED STATES PATENT AND TRADEMARK OFFICE
CERTIFICATE OF CORRECTION

PATENT NO. : 4,460,502

DATED : July 17, 1984

INVENTOR(S) : Kitaura et al.

It is certified that error appears in the above-identified patent and that said Letters Patent is hereby corrected as shown below:

- - [75] Inventors: Yoshihiko Kitaura, Sakurai; Osamu Nakagute, Toyonaka; Keiji Hemmi, Suita; Satoshi Yonishi, Kadoma; Hidekazu Takeno, Tenri; Satoshi Okada, Takatsuki; Masashi Hashimoto, Takarazuka, all of Japan - -

Signed and Sealed this

Twenty-sixth Day of February 1985

[SEAL]

Attest:

DONALD J. QUIGG

Attesting Officer     Acting Commissioner of Patents and Trademarks